(12) United States Patent
Cochran et al.

(10) Patent No.: US 8,097,857 B2
(45) Date of Patent: Jan. 17, 2012

(54) APPARATUS AND METHOD FOR PROVIDING SNAPSHOT ACTION THERMAL INFRARED IMAGING WITHIN AUTOMATED PROCESS CONTROL ARTICLE INSPECTION APPLICATIONS

(75) Inventors: Don W. Cochran, Novelty, OH (US); Steven D. Cech, Aurora, OH (US)

(73) Assignee: Pressco Technology Inc., Cleveland, OH (US)

(*) Notice: Subject to any disclaimer, the term of this patent is extended or adjusted under 35 U.S.C. 154(b) by 908 days.

(21) Appl. No.: 10/526,799

(22) PCT Filed: Aug. 21, 2002

(86) PCT No.: PCT/US02/95385
§ 371 (c)(1),
(2), (4) Date: Dec. 23, 2005

(87) PCT Pub. No.: WO02/095382
PCT Pub. Date: Nov. 28, 2002

(65) Prior Publication Data
US 2006/0232674 A1    Oct. 19, 2006

Related U.S. Application Data

(60) Provisional application No. 60/292,421, filed on May 21, 2001.

(51) Int. Cl.
*G01F 23/00* (2006.01)
(52) U.S. Cl. .................................................. 250/358.1
(58) Field of Classification Search ............... 250/358.1
See application file for complete search history.

(56) References Cited

U.S. PATENT DOCUMENTS

| | | |
|---|---|---|
| 3,748,137 A | 7/1973 | Worth et al. |
| 4,602,158 A | 7/1986 | Barrett |
| 4,689,246 A | 8/1987 | Barrett |
| 4,704,660 A * | 11/1987 | Robbins ..................... 362/552 |
| 4,760,444 A | 7/1988 | Nielson et al. |
| 4,806,761 A | 2/1989 | Carson et al. |
| 4,814,870 A * | 3/1989 | Crall .......................... 348/168 |
| 4,866,276 A | 9/1989 | Leavens et al. |

(Continued)

FOREIGN PATENT DOCUMENTS

CA    2 317 906 A1    4/2001

(Continued)

OTHER PUBLICATIONS

Supplementary European Search Report Sep. 7, 2010.

(Continued)

*Primary Examiner* — David Porta
*Assistant Examiner* — Mindy Vu
(74) *Attorney, Agent, or Firm* — Fay Sharpe LLP

(57) ABSTRACT

This application relates to an apparatus and method for providing snapshot action thermal infrared imaging within automated process control article inspection applications. More specifically, it pertains to the use of snapshot mode lead salt area-array imaging sensors (20) as the imaging front-end in high-speed machine vision inspection systems (12). the relatively low-cost, good measurement sensitivity at temperatures consistent with thereto-electric cooling means, and the ability to be operated in snap-shot mode enables lead salt-based image acquisition sensors (20) to be used in a variety of automated process control and article inspection applications.

39 Claims, 5 Drawing Sheets

U.S. PATENT DOCUMENTS

| | | | |
|---|---|---|---|
| 4,875,100 A | 10/1989 | Yonemoto et al. | |
| 4,882,498 A | 11/1989 | Cochran et al. | |
| 5,021,663 A | 6/1991 | Hornbeck | |
| 5,286,976 A | 2/1994 | Cole | |
| 5,420,419 A | 5/1995 | Wood | |
| 5,489,776 A | 2/1996 | Lung | |
| 5,631,465 A | 5/1997 | Shepard | |
| 5,677,533 A | 10/1997 | Yaktine et al. | |
| 5,711,603 A | 1/1998 | Ringermacher et al. | |
| 5,814,840 A * | 9/1998 | Woodall et al. | 257/103 |
| 5,887,073 A | 3/1999 | Fazzari et al. | |
| 5,936,353 A | 8/1999 | Triner et al. | |
| 6,013,915 A | 1/2000 | Watkins | |
| 6,137,116 A | 10/2000 | Amir et al. | |
| 6,346,704 B2 | 2/2002 | Kenway | |
| 6,353,197 B1 | 3/2002 | Ulrichsen et al. | |
| 2002/0011570 A1 * | 1/2002 | Castleman | 250/339.15 |
| 2002/0089561 A1 * | 7/2002 | Weitzel et al. | 347/19 |
| 2003/0222002 A1 * | 12/2003 | Meyer et al. | 209/630 |
| 2004/0003680 A1 * | 1/2004 | Wasmund et al. | 75/362 |

FOREIGN PATENT DOCUMENTS

| | | |
|---|---|---|
| JP | 61-102772 | 5/1986 |
| JP | 04-282445 | 10/1992 |
| JP | 07-333174 | 12/1995 |
| JP | 8-35884 | 2/1996 |
| JP | 8-297100 | 11/1996 |
| JP | 10-5229 | 1/1998 |
| JP | 10-142179 | 5/1998 |
| JP | 10-318955 | 12/1998 |
| JP | 11-214668 | 8/1999 |
| JP | 11-354762 | 12/1999 |
| JP | 2000-88781 | 3/2000 |
| JP | 2000-227407 | 8/2000 |
| JP | 2000-231875 | 8/2000 |

OTHER PUBLICATIONS

International Search Report corresponding to International Application No. PCT/US02/16194 Sep. 6, 2002.

* cited by examiner

APPARATUS AND METHOD FOR PROVIDING SNAPSHOT ACTION THERMAL INFRARED IMAGING WITHIN AUTOMATED PROCESS CONTROL ARTICLE INSPECTION APPLICATIONS

This application is based on and claims priority to U.S. Provisional Patent Application No. 60/292,421, filed May 21, 2001.

BACKGROUND OF THE INVENTION

This application relates to an apparatus and method for providing snapshot action thermal infrared imaging within automated process control article inspection applications. More specifically, it pertains to the use of snapshot mode lead salt area-array imaging sensors as the imaging front-end in high-speed machine vision inspection systems. The use of lead salt-based image acquisition sensors in a snapshot or stop-action mode allows for a wide variety of automated process control or article inspection applications.

While the invention is particularly directed to the art of high-speed automated product inspection, and will be thus described with specific reference thereto, it will be appreciated that the invention may have usefulness in other fields and applications. For example, the invention may be used in other applications where snapshot action is desired in a high-speed control process.

By way of background, the use of camera or video-based automated inspection techniques to aid in the quality or process control operations of manufacturers or producers is well known in the art. For example, U.S. Pat. No. 4,760,444 entitled "Machine Visual Inspection Device and Method" describes a device and method related to camera-based machine visual inspection of toothbrushes. This patent discusses the use of a fluorescent lamp to illuminate the target. It also references the camera measuring the reflectance data of the inspection field/toothbrush. As a further example of the state-of-the-art, U.S. Pat. No. 4,882,498 discusses the use of pulsed LED illumination to inspect specimens.

Typical in many of the prior art implementations of automated inspection, charge-coupled-device (CCD) based cameras are used. For example, U.S. Pat. No. 4,875,100 entitled "Electronic Shutter for a CCD Image Sensor" describes an innovation to the prior art architecture of CCD devices which extends its functionality to include an electronic shutter capability. This additional function allows CCD-based video imagers to provide "stop action" functionality where the action is occurring in rapidly changing image scenes without the need for synchronized, pulsed illumination. Many subsequent implementations of automated machine vision systems are known which are CCD-based.

The need to limit and synchronize in time the acquisition of imaged signal photons is a fundamental requirement of high-speed automated inspection. This statement is true independent of the wavelength of operation of the chosen image sensor used in a particular machine vision application. Cameras that are operable in the thermal IR region of the electromagnetic spectrum (between 2 and 12 um) and possess the ability to stop the action of rapidly evolving spatial scenes are currently known to exist. For example, the Radiance HSX High Performance Imaging Camera manufactured by Raytheon Corporation is purported to support snapshot mode acquisition. There are, however, several drawbacks to using this type of camera in machine vision applications and thus commercial deployment of thermal IR cameras in machine vision applications has been difficult. These drawbacks include the high-price and lack of ruggedness associated with a Stirling-cycle cooled, Indium Antimonide-based camera of this type.

A relatively new class of thermal infrared cameras/sensors has recently become available. This class of infrared imagers can generically be described as microbolometer-based devices. Key attributes of microbolometer-based thermal IR imagers include the fact that they do not require cryogenic cooling in order to operate as well as the fact that they can be fabricated using standard silicon CMOS IC fabricating equipment and processes. These attributes help to eliminate the high cost and lack of ruggedness associated with historical infrared imaging techniques. U.S. Pat. No. 5,021,663 entitled "Infrared Detector" and U.S. Pat. No. 5,286,976 entitled "Microstructure Design for High IR Sensitivity" describe the construction of suitable bolometer pixel-sites and pixel array deployments suitable for the detection of spatially varying thermal infrared signals. U.S. Pat. No. 5,489,776 entitled "Microbolometer Unit Cell Signal Processing Circuit" shows how other signal processing functions (in addition to the signal detection function) can be incorporated on a per-pixel basis using standard and well known CMOS fabrication processes. This patent describes the use of capacitor and transistor components as well as electrical interconnects all fabricated within the silicon-based microbolometer cell. These pixel site structures are used to convert the received thermal energy into ordered electrical signals representative of the scene that has been imaged onto the surface of the microbolometer array. U.S. Pat. No. 5,420,419 entitled "Camera for Producing Video Output Signal, Infrared Focal Plane Array Package for Such Camera, and Method and Apparatus for Generating Video Signals from Passive Focal Plane Array of Elements on a Semiconductor Substrate" describes one manner in which existing microbolometer imaging arrays can be deployed within an operating infrared camera.

Despite the body of knowledge that is available, none of the state-of-the-art microbolometer devices have been implemented in a manner that addresses the specific pixel-level functionality required for snapshot mode image acquisition. In addition, the inherent pixel-site response time and measurement sensitivity associated with microbolometer technology does not currently meet the requirements associated with very short signal integration, snapshot mode acquisition.

Single element lead salt detectors, in particular lead sulfide (PbS) and lead selenide (PbSe), have been used for decades in various applications involving the detection of infrared energy. Useful detection sensitivities are possible when one operates lead salt detectors at room temperature. Improved sensitivity is achieved as the device operational temperature is lowered and, in many applications involving lead salt detectors, 1 or 2 stage thermo-electric coolers are used.

However, the use of costly and undesired cryogenic cooling is not required when using this class of thermal IR detector. Moreover, in recent years, the ability to closely merge or integrate active two-dimensional arrays of lead salt photosites with silicon-based control electronics has made it possible to begin fabricating large area two-dimensional IR imaging arrays out of PbS and PbSe.

The lack of a cost-effective snapshot mode thermal IR camera possessing adequate temperature resolution performance without requiring cryogenic cooling has limited the application of thermal IR imaging front-ends within state-of-the-art machine vision systems. The disclosed invention contemplates a system and method for overcoming the known limitations.

SUMMARY OF THE INVENTION

The present invention is directed to a system and method of inspecting articles that finds particular application where the articles are produced and/or presented at high rates of dynamic speed by a conveyance device. The system includes an image processing subsystem configured to receive imagery from a camera or imager subsystem and to produce a summary status report of the quality or acceptance level of the article associated with the received image.

In one aspect of the invention, the camera or imager subsystem associated with the invention is based on the operation of a lead salt area array specifically configured to support snapshot mode image acquisition.

An advantage of the present invention is the ability to provide low-cost, on-line surface and sub-surface inspection of articles within a portion of the thermal IR portion of the electromagnetic spectrum (2 to 5 um).

Another advantage of the present invention is the ability to provide a very robust structural integrity inspection capability for articles and items which are generally transparent within the visible and near IR portion of the electromagnetic spectrum.

Another advantage of the present invention is the ability to provide high sensitivity, high speed, infrared imaging without implementing costly or non-robust cooling techniques.

Yet another advantage of the present invention is the ability to provide automated, low-cost temperature profiling of articles.

Further scope of the applicability of the present invention will become apparent from the detailed description provided below. It should be understood, however, that the detailed description and specific examples, while indicating preferred embodiments of the invention, are given by way of illustration only, since various changes and modifications within the spirit and scope of the invention will become apparent to those skilled in the art.

DETAILED DESCRIPTION OF THE DRAWINGS

The present invention exists in the construction, arrangement, and combination of the various parts of the device, and steps of the method, whereby the objects contemplated are attained as hereinafter more fully set forth and illustrated in the accompanying drawings in which.

Figure 3A:
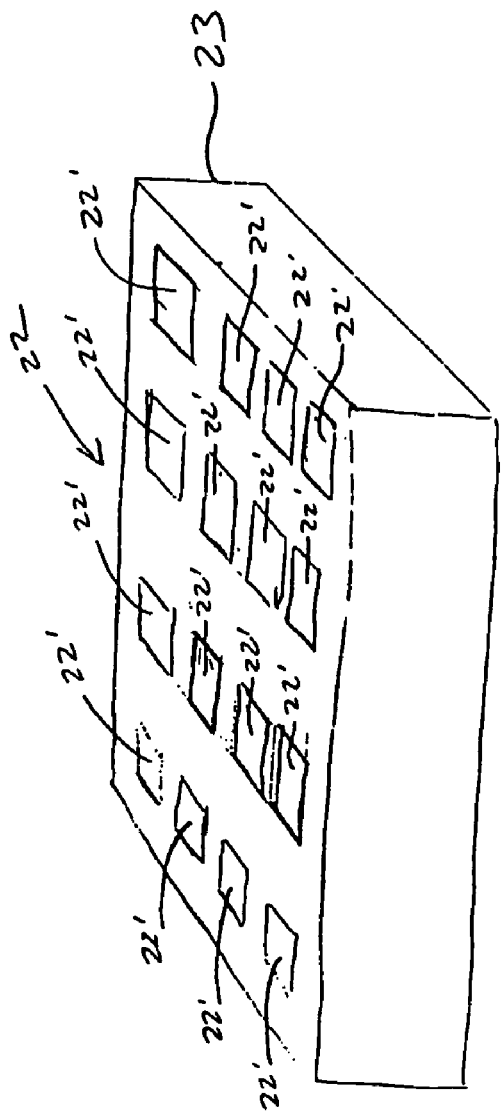
Figure 4:
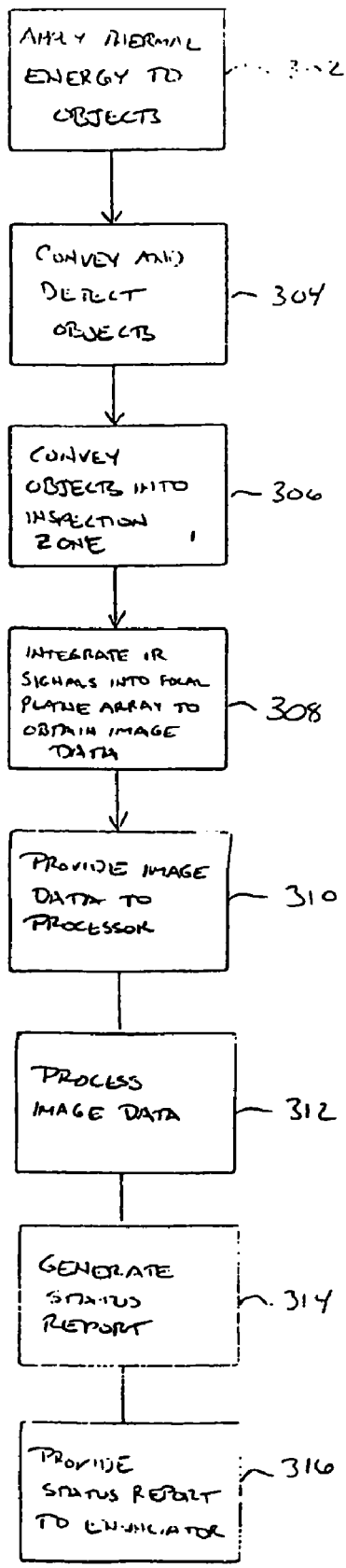

FIGS. 3(a) and (b) are block diagrams of an array and a single pixel site of a candidate thermal imager according to the present invention; and, FIG. 4 is a flow chart illustrating a method according to the present invention.

DETAILED DESCRIPTION OF THE INVENTION

Figure 1:
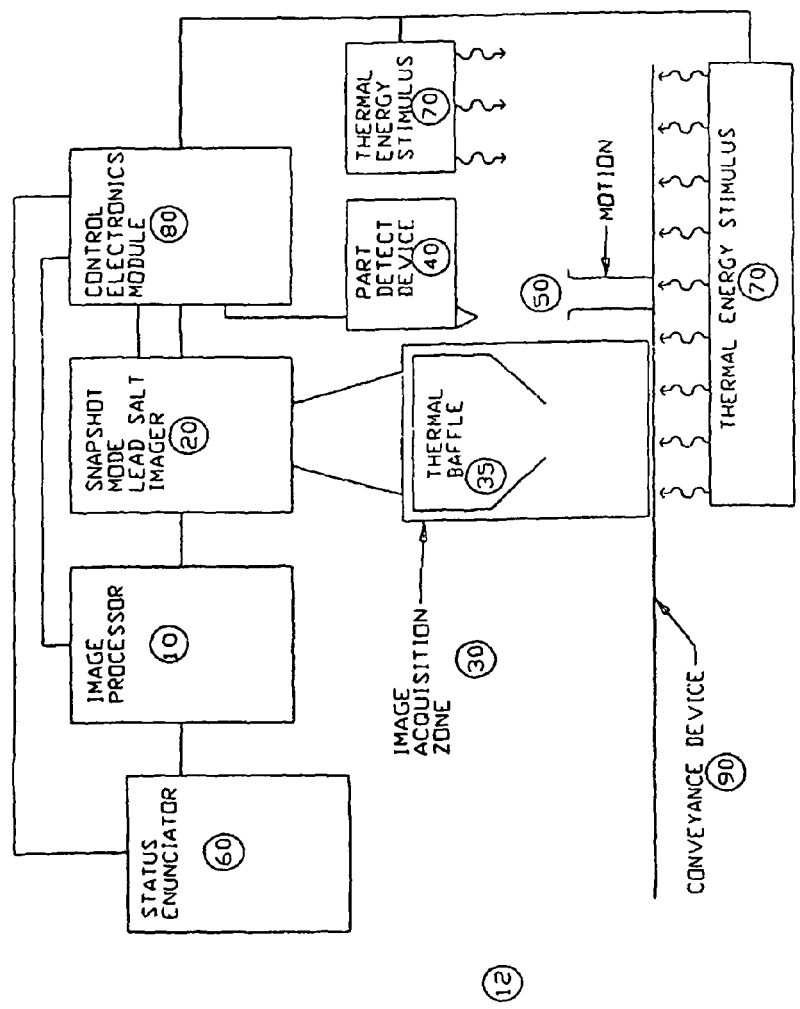
FIG. 1 is a block diagram illustrating a system according to the present invention.

Referring now to the drawings wherein the showings are for purposes of illustrating preferred embodiments of the invention only and not for purposes of limiting same, FIG. 1 provides a view of an overall preferred system 12 according to the present invention. As shown, an imager, preferably a snapshot mode lead salt imager, 20 is positioned to obtain infrared image data of objects or articles 50 under test as such objects move under the influence of a conveyance device 90 through a designated image acquisition zone 30. A control electronics module 80 acts to coordinate the operations of the functional components contained within the system such as an imager processor 10, a status enunciator 60, a thermal energy stimulus 70, the imager 20, and a part detection device 40. The part detection device 40 detects the presence of an object, or article, 50 as it moves toward the image acquisition zone 30.

In one preferred embodiment, the thermal energy stimulus 70 is provided to impart appropriate thermal energy to the objects or articles being inspected. Of course, in the event that the articles are of a character to store and subsequently emit sufficient and acceptable thermal energy for inspection by virtue of, for example, the production process or the like, no stimulus is necessary. Preferably, however, the thermal energy stimulus 70, which is illustrated as having two components disposed opposite one another relative to the conveyance device 90, performs a function analogous to the one performed by lighting systems contained in traditional machine vision systems. That is, the thermal energy stimulus 70 provides the stimulus that differentiates defective articles from ones that are acceptable. The successful application of controlled lighting stimuli to the objects being inspected is an attribute typically associated with the success of at least some of the traditional inspection applications. One preferred thermal energy stimulus thus applies controlled, consistent thermal energy to objects 50 under test to enhance the thermal infrared imaging features within machine vision applications and systems, such as that described in connection with the present invention.

In a preferred form, the imager 20 is a 1 or 2-dimensional array of lead salt photosites designed to be sensitive to a range of approximately 2 to 5 um of thermal infrared energy that is imaged onto its surface. Preferably, the lead salt is lead sulfide (PbS) or lead selenide (PbSe). This snapshot mode lead salt imager 20 preferably integrates or acquires thermal infrared photons in all of its pixels or cells simultaneously, thus supporting stop action imaging. The array preferably meets typical requirements associated with industrial machine vision applications, e.g. low-cost, ruggedness, fast response time, good sensitivity to support snapshot mode signal integration, and the absence of cryogenic cooling.

There are a variety of ways to access image data that is acquired using a 1 or 2-dimensional imaging array. One technique is to dedicate the appropriate signal processing resources that are required to support image formation to each and every pixel within the array. In this case, every pixel site within the array includes the necessary resources to perform functions such as current or charge-to-voltage conversion or analog-to-digital conversion. An output pin or port for each pixel within the array is also provided.

Such a configuration is acceptable for arrays having a very small number of total pixels. However, it is less practical for larger arrays. In these instances, it is preferable to utilize a single set of output resources (sometimes 2, 4, or 8 output ports are used) and then multiplex or switch the individual pixels sites to those resources in sequential fashion. One implication of using a multiplexer output architecture for snapshot mode signal integration is that there nonetheless needs to be included in the sensor design some type of per pixel signal storage means. In this regard, suitable integrated circuitry may be fabricated within independent silicon chips to perform the required per pixel charge storage and multiplexing functions, as is well known in the art. Similar techniques are used to create the silicon-based image sensors used in traditional machine vision systems.

By closely linking the photon-induced current or charge generated within the lead salt infrared photocells with a suitable silicon-based signal processing/readout circuit (described above), a viable snapshot mode thermal infrared imager is realized. Candidate methods of linking the photon-generated signal created within the lead salt photocells with the silicon readout circuitry include direct deposition of the lead salt compound onto silicon readout circuitry or, alternately, the use of indium bump bonding techniques to tie the lead salt focal plane to a silicon readout circuit. This general advancement in camera and acquisition technology enables the novel application of thermal IR camera front-ends within on-line machine vision systems, according to the present invention.

Figure 2:
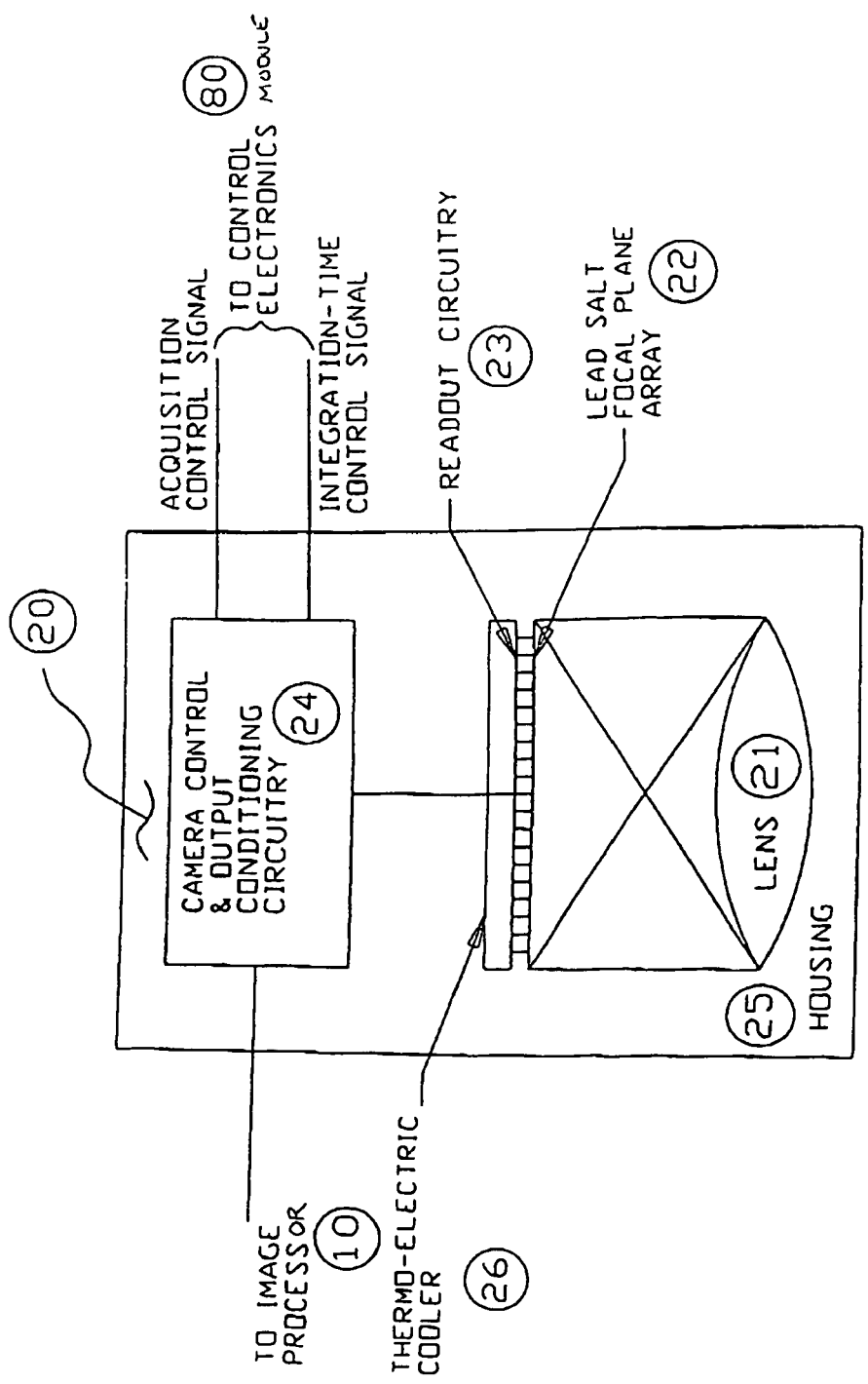
FIG. 2 is a block diagram illustrating an imager according to the present invention.

Referring now to FIG. 2, one preferred imager 20 includes a housing 25 which has positioned therein a lens 21, a lead salt focal plane array 22, and suitable readout circuitry 23. Also included within the housing 25 is a camera control and output conditioning circuit 24. Connections to the image processor 10 and the control electronics module 80 are also illustrated.

The housing 25 may take a variety of forms but preferably is of such configuration to support the components shown in FIG. 2. In addition, the housing 25 is also preferably of such character that it provides adequate thermal stability for the focal plane array 22 to accommodate adequate imaging.

Likewise, the lens 21 may be of various configurations. Lenses that provide adequate focussing of infrared signals are well known. However, it should be understood that the particular lens used may depend on the configuration of the focal plane array as well as the field-of-view requirements of the application.

The array 22 and readout circuitry 23 preferably are configured as described above. The camera control and output conditioning circuitry 24 is configured to process data (e.g. electrical signals) from the readout circuitry and also communicate with the control electronics module 80 and the image processor 10.

In operation, the lens 21 receives infrared signal photons from an article or object 50 that is emanating thermal energy and focuses these photons on the array 22. The pixels of the focal plane array 22 integrate the signal photons and convert the signal photons to electrical signals. These electrical signals are accessed in an orderly fashion by the readout circuitry 23 and handed off as input to the camera control and output conditioning circuitry 24. The circuitry 24 then provides an output signal (e.g. image data such as a two-dimensional infrared spatial image or data set) to the image processor 10 based on the electrical signals. It is to be appreciated that the control and output conditioning circuitry 24 also receives an acquisition control signal and an integration time control signal from the control electronics module 80.

A thermo-electric cooling device 26, which may take a variety of forms, is preferably deployed within the imager 20 as is indicated in FIG. 2. The primary function of the device 26 is to keep the focal plane array 22 at a stable operating temperature. This has the advantageous effect of improving the image acquisition performance of the imager 20. It should be understood that useful detection sensitivities are achievable when using lead salt detectors at room temperatures. Furthermore, improved measurement sensitivity is achieved as the detector's operational temperature is lowered. As such, a useful imager 20 could potentially be constructed wherein the focal plane array 22 is set at an operational temperature anywhere within the range from room to cryogenic temperatures. In keeping with the general scope of this invention, a preferable tradeoff between imager cost, lifetime, and measurement sensitivity is achieved when the focal plane array 22 is operated at temperatures consistent with 2 or 3 stage solid-state thermo-electric cooling components. The application of thermo-electric coolers is well known in the art.

Figure 3B:
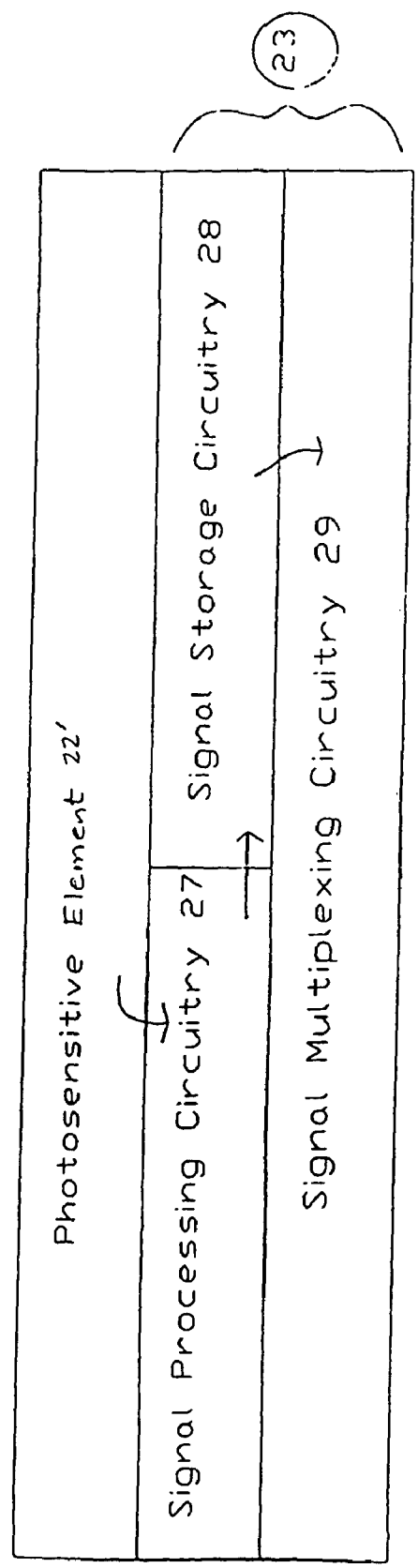

A more detailed description of the functional and physical flow of signal photons onto the focal plane array 22 and the resulting flow of image signals out of the readout circuitry 23 is provided in FIGS. 3(a) and (b). In FIG. 3(a), an exemplary array 22 is shown as having a plurality of photosensitive elements 22', positioned on the readout circuitry 23. The number of elements 22' will, of course, vary from system to system. The array shown is an example for illustration purposes only—a typical number of elements 22' would be of much higher magnitude. Referring to FIG. 3(b), which shows a single pixel photosite of the array, signal induced changes occurring within a pixel photosite are directed from the photosensitive element 22' formed of lead-salt and into the silicon-based signal processing region 27 contained within the pixel site. This signal is used to convert the signal-induced electronic change occurring within the photosensitive array 22 into a form which can first be stored in the signal storage 28 portion of the pixel and then, later, shifted out of the pixel array using the signal multiplexing circuitry 29. It is to be appreciated as described above, that the circuitry 27 and 28 is required to be provided for each photosite uniquely where as the multiplexing circuitry is provided to multiplex the signals from all photosites in a form to reduce circuitry. This functional description is provided here to show, for illustrative purposes, the general functionality of a candidate thermal imager. In no way should it be interpreted to limit the scope of the disclosed invention to focal plane array and readout circuitry implementations meeting this specific description.

With reference back now to FIG. 1, the image acquisition zone 30 may take a variety of forms to support the preferred snapshot mode image acquisition. For example, it may simply be an area along the conveyer device 90 that is particularly conducive to detection by the imager 20. Alternatively, the zone 30 may comprise a housing or tunnel into which inspected parts are conveyed. Given the character of a preferred system, the inspection zone preferably comprises a radiation baffle structure 35 which acts to block, or shield, deleterious energy such as undesired, stray or specific thermal radiation such as that emanating from uncontrolled or non-preferred sources from reflecting off of the inspected part 50 and into the field-of-view of the imager 20. Of course, desired thermal radiation would not be blocked by the structure 35 shown nor would desired radiation be blocked in a variety of other configurations that will be apparent to those skilled in the art. Moreover, the baffle structure 35 provides an improved signal to noise ratio. In some cases, the baffle structure 35 may improve the signal to noise ratio such that it differentiates systems having acceptable performance from those systems having unacceptable performance. Additionally, the baffle structure 35 contained in the inspection zone 30 should have the properties of high thermal absorption as well as a relatively low self-emission. These properties are preferably achieved by using a radiation baffle 35 possessing a high surface emissivity which is then cooled in some manner (for example, through the use of thermo-electric coolers) to a temperature significantly below the temperature of the inspected part 50 or monitored process. It is to be appreciated that the baffle structure 35 may take a variety of forms to achieve the objectives of the invention.

The image processor 10 may also take a variety of forms. Image processors that are capable of processing image data in electrical or digital format are well known in the art. Further, image processors that analyze image data and determine characteristics of the image based on predetermined criteria are likewise well known. A suitable image processor for implementing the present invention should be capable of achieving the objectives of the invention as described herein but otherwise may be of any known type.

In one preferred embodiment, the part detection device 40 is an opto-electronic type switch which is well known within the industry. However, it could equally be any type of sensor component capable of detecting the presence of an article 50 under test and electronically communicating this condition to the control electronics module 80.

The article or object 50 may take the form of any article that can be suitably conveyed and inspected, preferably at high speed in an automated process control environment. For example, the objects may be containers of varying configuration. However, the articles or objects 50, of whatever form, are preferably of such nature so as to store and emit thermal energy that is generated in the production process or through the implementation of a thermal energy stimulus, such as that designated by 70.

In one preferred embodiment, the status enunciator 60 is a type of mechanical reject means such as an air valve or solenoid which acts to remove articles from their normal dynamic flow whenever the image processor 10 determines them to be below a predefined quality level. Alternately, the status enunciator 60 could be implemented as a print or display report writer that acts to provide a part-by-part quality report and/or cumulative archive of article quality. As a further alternative, the status enunciator is implemented as a marking device which acts to mark in some prescribed fashion articles whenever they are determined to be below or, alternatively, above a predefined quality level.

Various manners and devices for adding thermal energy to objects under test are known at this time. As such, the thermal energy stimulus 70 may take a variety of forms. Known techniques include the use of induction principles (e.g. induction type heater), ultrasonic waves (e.g. ultrasonic heater) and microwaves. Blackbody emitters such as lamps (e.g. a quartz halogen lamp) and glowbars with energy being exchanged by way of natural convection and/or forced air flow. Other devices that would be suitable include quartz lights, infrared emitters, ovens, high-powered lasers (e.g. a spatially directed high-powered laser) and directable ultrasonic devices. Thermal energy may also be added to the object 50 under test by way of energizing any active electrical components associated with the part. Examples of parts which can be advantageously stimulated with electrical self-heating include motors, transformers, and electronic circuit boards. Though one preferred embodiment includes provisions for the application of controlled thermal energy to the object 50 under test, it should be understood that the spirit of the invention includes those application areas wherein the normally occurring thermal energy contained within the part that results from one or more steps of the normal manufacturing process is alone sufficient for defective attribute detection. Similarly, the invention also includes the implementation of devices that would primarily be directed to ensuring that thermal energy within the inspected objects is appropriately distributed within the object to improve the imaging thereof.

In a similar fashion, though one preferred embodiment discusses the use of a snapshot mode lead salt imager 20 to acquire images from objects which are in motion, it should be understood that such an imager deployed properly within a machine vision system would also be useful in acquiring imagery of static objects. In particular, the ability of such an infrared camera to tailor its image acquisition operations to demanding acquisition and integration duration signals allows it to acquire useful information of dynamic thermal events occurring in objects of interest. An example where time critical imaging operations occurring within the thermal infrared might be of use in determining the acceptability of manufactured product includes the inspection of operational electronic assemblies under dynamic power up conditions. The ability to instruct the camera to acquire imagery of the electronic circuit at predefined, tightly controlled time periods after the application of power to the assembly could allow some classes of defective operation to be observed.

The control electronics module 80 may take a variety of configurations (both in hardware and software) but preferably performs accurate timing functions based on the instantaneous motion of the conveyance device 90, or the instantaneous motion of the part being conveyed by the device 90, based on signaling from the part detect device 40 and applies image acquisition control signals such as an acquisition signal and an integration time signal to the snapshot mode lead salt imager 20.

The conveyance device 90 is preferably a conventional conveyor system having moving bands or belts that cause the objects to move. For example, the conveyance device may comprise an automated conveyance device used to dynamically present a stream of parts in rapid succession to the inspection/process control system. However, the system used preferably is configured to accommodate the thermal energy stimulus. It should also be understood that the conveyance device 90, while preferably conveying the objects into an inspection zone, may be replaced with a system whereby the imaging equipment is conveyed relative to the objects.

In one preferred operation, objects or articles 50 are conveyed along the conveyer device 90 and through a thermal energy stimulus 70. The article is then detected by the part detect device 40. Once the object 50 is within the image acquisition zone 30, the imager 20 acquires an image of the object as a result of the image acquisition signal that is generated by control electronics module 80 in response to a signal from the part detect device 40. This acquisition signal informs the imager 20 that a part is in the proper location within the image acquisition zone 30 and that the integration or collection of infrared signal photons should commence. The snapshot mode lead salt imager 20 preferably then begins simultaneously integrating signal photons in all of the pixels contained within its focal plane array (shown in FIG. 2) for a specified time period based on the integration time control signal.

Once the imager 20 has acquired signal photons for a predetermined exposure time, signal integration will be electronically terminated and the image data that has been collected is preferably handed off in some fashion to the image processor 10. The image processor 10 acts upon the image data provided by the imager 20 to produce a summary status report of the article associated with the received image. This summary status report is either directly or indirectly (via the control electronics module 80) communicated to the status enunciator 60 for action. That is, the image processor receives and processes the output of the thermal infrared imager in a manner which reduces the two-dimensional infrared spatial image or data set produced by the imager into a specific set of quality- or process-related attributes associated with the part or process under inspection.

More particularly, referring now to FIG. 4, one preferred method 300 reflecting basic steps of operation above is shown. Initially, thermal energy is applied to objects 50 under inspection prior to entering the inspection zone 30 (step 302). It is to be appreciated that thermal energy may be provided by the thermal energy stimulus 70 or may be inherent in the object as a result of a manufacturing or control process. Further, the stimulus may simply be provided to ensure that infrared energy is suitably distributed within the objects. The object is then conveyed and detected as it enters an inspection, or image acquisition, zone 30 (steps 304 and 306). The detecting is accomplished by the part detect device 40 which simultaneously sends a detection signal to the module 80.

Suitable signaling (i.e. an image acquisition signal and an integration time control signal) is then conveyed by the module 80 to the snapshot mode lead salt imager 20 based on the detection signal so that the infrared energy emitted by the object can be collected and the infrared signal photons can be integrated by the pixels of the focal plane array of the imager 20 for a predetermined time period to obtain suitable image data (step 308). This image data is then provided to the image processor 10 by the control circuitry 24 of the imager 20 (step 310). The image data is then processed by the image processor, using techniques that are well known in the art (step 312). The purposes of the processing may be to detect imperfections in the object, or simply to determine an overall status of the object. A status report is then generated based on the processing of the image data (step 314).

The status report is provided directly or indirectly (through, for example, the module 80) to the status enunciator 60 (step 316). It should be understood that once the status enunciator collects the status report, a variety of steps may then be undertaken. For example, if the purpose of the image acquisition was to detect defects in the objects being inspected, then the status enunciator may take the form of a part reject or accept device and proceed to reject the object by way of, for example, a mechanical reject device (such as an air valve or solenoid which acts to remove the article from the path of conveyance). Alternatively, the status enunciator may simply be implemented as a printing or displaying mechanism that acts to provide part-by-part quality reports and/or cumulative reports on the article quality. Further, the status enunciator may be implemented in other forms such as the marking device (noted above) or as a module that electronically communicates part or process status in a manner which facilitates closed loop control over the manufacturing process.

Though one preferred embodiment discusses the general advantages and implementation details associated with a broad band thermal IR inspection system, it should be recognized that an essentially similar system additionally deploying selective spectral filters with the front end of the imager 20 would also be useful in some instances. The ability to limit the systems sensitivity to specific wavelengths within the thermal IR region where important information related to the inspected part or process is known to exist tends to increase the overall signal-to-noise ratio of the system. This has the advantageous effect of making the decisions rendered by the system more accurate and reliable.

The description herein focuses on inspection and/or control processes relating to articles or objects 50. However, it should be appreciated that a system according to the present invention could also be used to monitor a complex process or system having a multiplicity of thermal areas of interest.

In addition, as described in one preferred embodiment, the data collected by the system is sufficient to render a decision on the acceptability of a part or process. However, it should be understood that the data collected by a system according to the invention may only comprise a portion of a data set used to render a decision.

The above description merely provides a disclosure of particular embodiments of the invention and is not intended for the purposes of limiting the same thereto. As such, the invention is not limited to only the above-described embodiments. Rather, it is recognized that one skilled in the art could conceive alternative embodiments that fall within the scope of the invention.

We claim:

1. A system for providing snapshot action thermal imaging within a high speed automated process control article inspection environment comprising:
    a lead salt-based thermal infrared imager configured to support snapshot-mode image acquisition in the high speed environment;
    an image acquisition zone configured to support the snapshot-mode image acquisition of a part or process being presented at a high rate of speed;
    an image processor configured to receive and process output of the imager in a manner which reduces a two-dimensional infrared spatial image or data set produced by the imager into a specific set of quality- or process-related attributes associated with the part or process within the image acquisition zone; and,
    a control electronics module configured to provide image acquisition control signals within the system.

2. The system as set forth in claim 1 further comprising an automated conveyance device used to dynamically present a stream of parts in rapid succession to the system.

3. The system as set forth in claim 2 further comprising a part detect or presence sensing device which interfaces to the control electronics module and provides the system an indication of the presence of a part requiring inspection.

4. The system as set forth in claim 1 further comprising a thermal baffle disposed within the inspection zone to shield the imager from deleterious thermal infrared energy emanating from uncontrolled or non-preferred sources.

5. The system as set forth in claim 4 wherein the thermal baffle comprises high emissivity surfaces to facilitate absorption of the deleterious thermal infrared energy.

6. The system as set forth in claim 5 wherein the thermal baffle is actively cooled to reduce self-emission of thermal infrared energy.

7. The system as set forth in claim 6 wherein the thermal baffle is cooled using thermo-electric coolers.

8. The system as set forth in claim 1 further comprising a thermal energy stimulus used for imparting thermal energy to the part or process for differentiating defective parts from acceptable parts.

9. The system as set forth in claim 8 wherein the thermal energy stimulus is implemented as an induction-type heater.

10. The system as set forth in claim 8 wherein the thermal energy stimulus is implemented as an ultrasonic heater.

11. The system as set forth in claim 8 wherein the thermal energy stimulus is implemented as a microwave source.

12. The system as set forth in claim 8 wherein the thermal energy stimulus is implemented as a spatially-directed high power laser.

13. The system as set forth in claim 8 wherein the thermal energy stimulus is implemented as a blackbody emitter.

14. The system as set forth in claim 3 wherein the blackbody emitter is implemented as a lamp.

15. The system set forth in claim 14 wherein the lamp is implemented as a quartz halogen lamp.

16. The system as set forth in claim 14 wherein the thermal energy emitted by the lamp is exchanged by way of natural convection.

17. The system as set forth in claim 14 wherein the thermal energy emitted by the lamp is exchanged by way of forced air flow.

18. The system as set forth in claim 13 wherein the blackbody emitter is implemented as a glowbar.

19. The system as set forth in claim 18 wherein the energy emitted by the glowbar is exchanged by way of natural convection.

20. The system as set forth in claim 18 wherein the energy emitted by the glowbar is exchanged by way of forced air.

21. The system as set forth in claim 1 wherein thermal infrared energy is added to the part by electrically energizing components associated with the part.

22. The system as set forth in claim 1 further comprising a status enunciator used to indicate a status of the part or process under inspection.

23. The system as set forth in claim 22 wherein the status enunciator is implemented as a mechanical reject mechanism which acts to remove specific parts from a manufacturing process when such parts are determined to be below or, alternately, above a predefined quality level.

24. The system as set forth in claim 23 wherein the reject mechanism is an air valve.

25. The system as set forth in claim 23 wherein the reject mechanism is a solenoid actuator.

26. The system as set forth in claim 22 wherein the status enunciator is implemented as a marking device which acts to mark parts determined to be below or, alternately, above a predefined quality level.

27. The system as set forth in claim 22 wherein the status enunciator is implemented as a print or display report writer that acts to provide a part-by-part quality report.

28. The system as set forth in claim 22 wherein the status enunciator is implemented as a print or display report writer that acts to provide a cumulative archive of article quality.

29. The system as set forth in claim 22 wherein the status enunciator is implemented as a module that electronically communicates part or process status in a manner which facilitates closed loop control of a manufacturing process.

30. A method for providing snapshot action thermal infrared imaging within a high steed automated process control article inspection environment, the method comprising the steps of:
    simultaneously integrating thermal infrared signals within all pixel sites of a lead salt-based imager based on image acquisition control signals provided by an electronics control module;
    providing a two-dimensional infrared spatial image or data set based on the pixel site integrating to a processor; and,
    processing the two-dimensional infrared spatial image or data set into a set of quality- or process-related attributes associated with a part or process under inspection being presented at a high rate of speed.

31. The method as set forth in claim 30 further comprising the step of automatically conveying objects to be inspected into an inspection zone.

32. The method as set forth in claim 30 further comprising the step of applying thermal energy to parts under inspection for the purpose of differentiating defective parts from acceptable parts.

33. The method as set forth in claim 30 further comprising the step of generating a status report based on the processing.

34. The method as set forth in claim further comprising the step of proving the status report to a status enunciator.

35. The method as set forth in claim 34 further comprising the step of using the status report to automatically alter parameters of a manufacturing process.

36. A method for providing snapshot action thermal infrared imaging within a high speed automated process control article inspection environment, the method comprising the steps of:
    energizing components within an inspected part or process by applying a controlled voltage or current to the components;
    simultaneously integrating thermal infrared signals within all pixel sites of a lead salt-based imager based on image acquisition control signals provided by an electronics control module;
    providing a sequence of two-dimensional infrared spatial ages or data sets based on the pixel site integrating to a processor; and,
    processing the two-dimensional infrared spatial images or data sets into a set of quality- or process-related attributes associated with a part or process under inspection being presented at a high rate of speed.

37. The method as set forth in claim 36 further comprising the step of generating a status report based on the processing.

38. The method as set forth in claim 37 further comprising the step of providing the status report to a status enunciator.

39. The method as set forth in claim 38 further comprising the step of using the status report to automatically alter parameters of a manufacturing process.

* * * * *